United States Patent
Takahashi et al.

(10) Patent No.: US 11,899,832 B2
(45) Date of Patent: Feb. 13, 2024

(54) OBSERVATION STREAMLINING APPARATUS, OBSERVATION STREAMLINING METHOD AND PROGRAM

(71) Applicant: NIPPON TELEGRAPH AND TELEPHONE CORPORATION, Tokyo (JP)

(72) Inventors: Masami Takahashi, Tokyo (JP); Masahiro Kojima, Tokyo (JP); Takeshi Kurashima, Tokyo (JP); Hiroyuki Toda, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 0 days.

(21) Appl. No.: 17/799,598

(22) PCT Filed: Feb. 21, 2020

(86) PCT No.: PCT/JP2020/007229
§ 371 (c)(1),
(2) Date: Aug. 12, 2022

(87) PCT Pub. No.: WO2021/166253
PCT Pub. Date: Aug. 26, 2021

(65) Prior Publication Data
US 2023/0062607 A1    Mar. 2, 2023

(51) Int. Cl.
*G06F 15/16* (2006.01)
*G06F 3/01* (2006.01)
*H04L 67/12* (2022.01)

(52) U.S. Cl.
CPC ................ *G06F 3/01* (2013.01); *H04L 67/12* (2013.01)

(58) Field of Classification Search
CPC ........ G16H 20/30; G16H 20/60; G16H 50/20; H04L 67/12
See application file for complete search history.

(56) References Cited

U.S. PATENT DOCUMENTS

| 2007/0037610 A1* | 2/2007 | Logan | H04M 1/72448 |
| | | | 455/574 |
| 2012/0242788 A1* | 9/2012 | Chuang | H04N 23/62 |
| | | | 348/E7.001 |

(Continued)

FOREIGN PATENT DOCUMENTS

| JP | 2015131008 A | 7/2015 |
| JP | 2015191469 A | 11/2015 |
| JP | 2020000306 A | 1/2020 |

OTHER PUBLICATIONS

Rabbi, Mashfiqui et al. (2015) "Automated personalized feedback for physical activity and dietary behavior change with mobile phones: a randomized controlled trial on adults." JMIR mHealth and uHealth 3.2.

(Continued)

*Primary Examiner* — Hieu T Hoang

(57) ABSTRACT

An observation streamlining apparatus includes one or more computers each including a memory and a processor configured to discriminate between an observation-necessary time slot and an observation-unnecessary time slot with an intervention measure including at least a time when a predetermined intervention is performed on a user as an input, the observation-necessary time slot indicating a time slot when a user's action or state needs to be observed, and the observation-unnecessary time slot indicating a time slot when the user's action or state does not need to be observed; and execute predetermined processing for observing the user's action or state when the observation-necessary time slot arrives.

6 Claims, 13 Drawing Sheets

(56) References Cited

U.S. PATENT DOCUMENTS

| | | | | |
|---|---|---|---|---|
| 2012/0278478 | A1* | 11/2012 | Fujino | H04L 43/10 |
| | | | | 709/224 |
| 2014/0018636 | A1* | 1/2014 | Contant | A61B 5/1112 |
| | | | | 600/595 |
| 2014/0058801 | A1* | 2/2014 | Deodhar | G06Q 10/0639 |
| | | | | 705/7.38 |
| 2015/0106369 | A1* | 4/2015 | Nolan | H04L 51/046 |
| | | | | 707/732 |
| 2015/0199484 | A1* | 7/2015 | Morris | G16H 50/20 |
| | | | | 705/2 |
| 2016/0180695 | A1* | 6/2016 | Levchenko | G08B 21/245 |
| | | | | 340/573.1 |
| 2016/0203691 | A1* | 7/2016 | Arnold | A61B 5/681 |
| | | | | 340/539.12 |
| 2016/0235374 | A1* | 8/2016 | Miller | A61B 5/7275 |
| 2019/0335913 | A1* | 11/2019 | Tsern | G05D 23/1902 |

OTHER PUBLICATIONS

Park, Il Memming et al. (2013) "Kernel methods on spike train space for neuroscience: a tutorial." IEEE Signal Processing Magazine 30.4: pp. 149-160.

\* cited by examiner

Fig. 2

| TIME | USER ACTION |
|---|---|
| 9:00 | BREAKFAST |
| 10:00 | WORK |
| 11:45 | LUNCH |
| 13:00 | WORK |
| 15:30 | SNACK |
| ... | ... |

Fig. 3

| TIME | USER ACTION |
|---|---|
| 22:00 | SLEEP |
| ... | ... |

Fig. 4

| TIME | USER ACTION | INTERVENTION |
|---|---|---|
| 20:00 | DINNER | BATH |
| 20:00 | HOUSEWORK | BATH |
| 20:00 | HOBBY | RELAX |
| 20:00 | WORK | RELAX |
| 20:00 | SLEEP | NO INTERVENTION |
| ... | ... | ... |

Fig. 10

| LOG SEQUENCE | REWARD VALUE |
|---|---|
| 12:00 LUNCH, 13:00 WORK, 18:00 DINNER | 30.5 |
| 19:30 EXERCISE, 20:00 HOUSEWORK, 20:30 DINNER | 24.0 |
| 21:30 BATH, 22:00 RELAX | 45.8 |
| 22:00 HOUSEWORK | 31.0 |
| ... | ... |

OBSERVATION STREAMLINING APPARATUS, OBSERVATION STREAMLINING METHOD AND PROGRAM

CROSS-REFERENCE TO RELATED APPLICATIONS

This application is a U.S. National Stage Application filed under 35 U.S.C. § 371 claiming priority to International Patent Application No. PCT/JP2020/007229, filed on 21 Feb. 2020, the disclosure of which is hereby incorporated herein by reference in its entirety.

TECHNICAL FIELD

The present disclosure relates to an observation streamlining apparatus, an observation streamlining method and a program.

BACKGROUND ART

An increase in lifestyle-related diseases is a social issue, and many of them result from accumulation of unhealthy lifestyle habits. In order to prevent lifestyle-related diseases, it is effective to review one's lifestyle before getting sick and to adopt healthy habits such as adequate sleep, proper exercise, and regular eating habits.

Thus, in recent years, applications that dynamically promote users to perform some action such as sleep, relaxation, or exercise (that is, applications that dynamically perform intervention of promoting users to perform some action) have become known. In order to achieve such intervention, appropriate intervention is required to be determined while observing an action and state of a user (hereinafter, an action and a state of a user will be collectively referred to as a "user action") (NPL 1).

CITATION LIST

Non Patent Literature

NPL 1: Rabbi, Mashfiqui, et al. "Automated personalized feedback for physical activity and dietary behavior change with mobile phones: a randomized controlled trial on adults." JMIR mHealth and uHealth 3.2 (2015)

SUMMARY OF THE INVENTION

Technical Problem

However, in the related art, it is not possible to efficiently observe a user action. For example, in order to determine appropriate intervention, a system needs to observe a user action at all times, but a user action is not always possible to be observed. Further, in a case where a user action which is difficult for a system to recognize automatically is set to be an observation target, a user action needs to be described manually by a human.

An embodiment of the present disclosure has been made in view of the above-described circumstances, and an object thereof is to efficiently observe a user action.

Means for Solving the Problem

In order to accomplish the above-mentioned object, an observation streamlining apparatus according to an embodiment includes a discrimination unit that discriminates between an observation-necessary time slot, which indicates a time slot when a user's action or state needs to be observed, and an observation-unnecessary time slot, which indicates a time slot when the user's action or state does not need to be observed, with an intervention measure including at least a time when a predetermined intervention is performed on a user as an input, and an observation promotion unit that executes predetermined processing for observing the user's action or state when the observation-necessary time slot arrives.

Effects of the Invention

According to an aspect of the present invention, it is possible to efficiently observe a user action.

BRIEF DESCRIPTION OF DRAWINGS

FIG. 2 is a diagram illustrating an example of action log data in Example 1.
FIG. 3 is a diagram illustrating an example of goal data in Example 1.
FIG. 4 is a diagram illustrating an example of intervention measure data in Example 1.
FIG. 10 is a diagram illustrating an example of action log data in Example 2.

DESCRIPTION OF EMBODIMENTS

Hereinafter, an embodiment of the present disclosure will be described. In the present embodiment, an observation streamlining apparatus 10 capable of efficiently observing a user action is described. A user action is an action of the user, a state of the user, or the like.

Here, in the present embodiment, as an example, an application for performing intervention for promoting a user action (for example, "Why don't you have dinner soon? " or "It's time to go to bed") on a user's goal (for example, "sleep at 11 p.m." or the like) is assumed, and a case where a user action for appropriately determining such intervention is efficiently observed will be described. The intervention involves to promoting a user to perform some action. In the present embodiment, as an example, intervention is performed to promote a user to perform a user action. Note that such intervention is achieved by, for example, a reminder notification or the like.

Further, in the present embodiment, as an example, it is assumed that user actions are 1: sleep, 2: breakfast, 3: lunch, 4: dinner, 5: snack, 6: go to work, 7: work, 8: get off work, 9: housework, 10: exercise, 11: relax, 12: bath, 13: hobby, 14: drink, and 15: shopping. On the other hand, intervention (more precisely, a user action promoted by intervention) also includes 16: no intervention (none), in addition to 1 to 15 described above.

Example 1

Hereinafter, Example 1 will be described. In Example 1, a user action is assumed to be State, intervention by an agent (that is, a system such as an application) is assumed to be Action, and a user's goal is assumed to be Reward. In Example 1, a case where an optimal intervention measure (hereinafter referred to as an "intervention measure") is learned by model-based reinforcement learning, and then the efficiency of observation for determining an optimal intervention by the intervention measure is improved, will be described.

In the model-based reinforcement learning, environmental parameters such as a state transition probability are estimated, and then an intervention measure is estimated using the environmental parameters. In the following, a time slot having a predetermined time interval (in the present example, an interval of one hour) will be shown by assuming an index representing the time in reinforcement learning to be t. Specifically, it is assumed that t=0 represents a time slot of 0:00 to 0:59, t=1 represents a time slot of 1:00 to 1:59, . . . , and t=23 represents a time slot of 23:00 to 23:59.

Functional Configuration of Observation Streamlining Apparatus 10 (Example 1)

Figure 1:
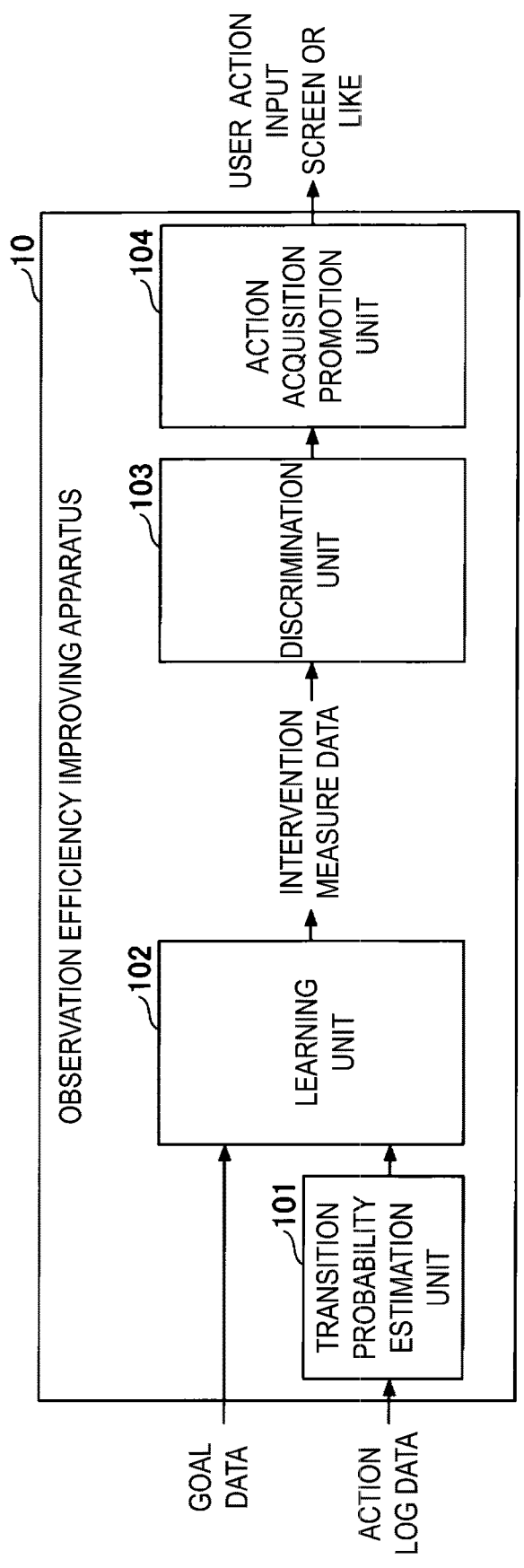
FIG. 1 is a diagram illustrating an example of a functional configuration of an observation streamlining apparatus according to Example 1.

First, a functional configuration of the observation streamlining apparatus 10 in Example 1 will be described with reference to FIG. 1. FIG. 1 is a diagram illustrating an example of the functional configuration of the observation streamlining apparatus 10 in Example 1.

As illustrated in FIG. 1, the observation streamlining apparatus 10 in Example 1 includes a transition probability estimation unit 101, a learning unit 102, a discrimination unit 103, and an action acquisition promotion unit 104.

The transition probability estimation unit 101 estimates a state transition probability in the model-based reinforcement learning, with action log data representing a log of user actions collected in advance, as an input.

The learning unit 102 estimates intervention measure data representing an optimal intervention measure, with goal data representing a user's goal and the state transition probability estimated by the transition probability estimation unit 101, as inputs.

The discrimination unit 103 discriminates between a time slot in which it is necessary to observe a user action (hereinafter referred to as an "observation-necessary time slot") and a time slot in which it is unnecessary to observe a user action (hereinafter referred to as an "observation-unnecessary time slot") with the intervention measure data estimated by the learning unit 102, as an input. Specifically, the discrimination unit 103 determines a time slot in which an optimal intervention varies depending on a user action to be the observation-necessary time slot, and determines a time slot in which an optimal intervention is identical regardless of a user action to be the observation-unnecessary time slot.

The action acquisition promotion unit 104 performs various processing operations for observing a user action during the observation-necessary time slot.

For example, the action acquisition promotion unit 104 displays a screen for promoting a user to input a user action (hereinafter referred to as a "user action input screen") on a terminal or the like that is used by the user. In addition, the action acquisition promotion unit 104 may output, for example, an alert for promoting the user to input a user action to the terminal or the like. In addition, for example, the action acquisition promotion unit 104 may make a frequency of promoting a user to input a user action vary between an observation-necessary time slot and an observation-unnecessary time slot (that is, an input is promoted at a high frequency during the observation-necessary time slot, while an input is promoted at a low frequency during the observation-unnecessary time slot, or the like). Further, for example, in a case where a user action can be automatically observed by a sensor or the like, the action acquisition promotion unit 104 may observe a user action during the observation-necessary time slot but may not observe a user action during the observation-unnecessary time slot. In addition, for example, in a case where a user forgets to input a user action during the observation-necessary time slot or in a case where a user action cannot be observed due to a sensor error or the like during the observation-necessary time slot, the action acquisition promotion unit 104 may output the above-mentioned alert to the terminal or the like.

Note that, in the present embodiment, a case where the action acquisition promotion unit 104 displays a user action input screen on the terminal or the like will be described as an example.

Here, an example of action log data in Example 1 will be described with reference to FIG. 2. FIG. 2 is a diagram illustrating an example of action log data in Example 1.

As illustrated in FIG. 2, the action log data in Example 1 is data in which a time is associated with a user action that is actually performed by a user. In the example illustrate in FIG. 2, a time "9:00" is associated with a user action "breakfast", a time "10:00" is associated with a user action "work", a time "11:45" is associated with a user action "lunch", a time "13:00" is associated with a user action "work", and a time "15:30" is associated with a user action "snack". They indicate that the user is performing the user action "breakfast" between 9:00 and 10:00, the user is performing the user action "work" between 10:00 and 11:45, the user is performing the user action "lunch" between 11:45 and 13:00, and the user is performing the user action "work" between 13:00 and 15:30.

In this manner, the action log data in Example 1 is data in which a user action that is actually performed by the user is associated with a time when the user action is performed. Such action log data is collected in advance before a state transition probability in model-based reinforcement learning is estimated.

Figure 3:
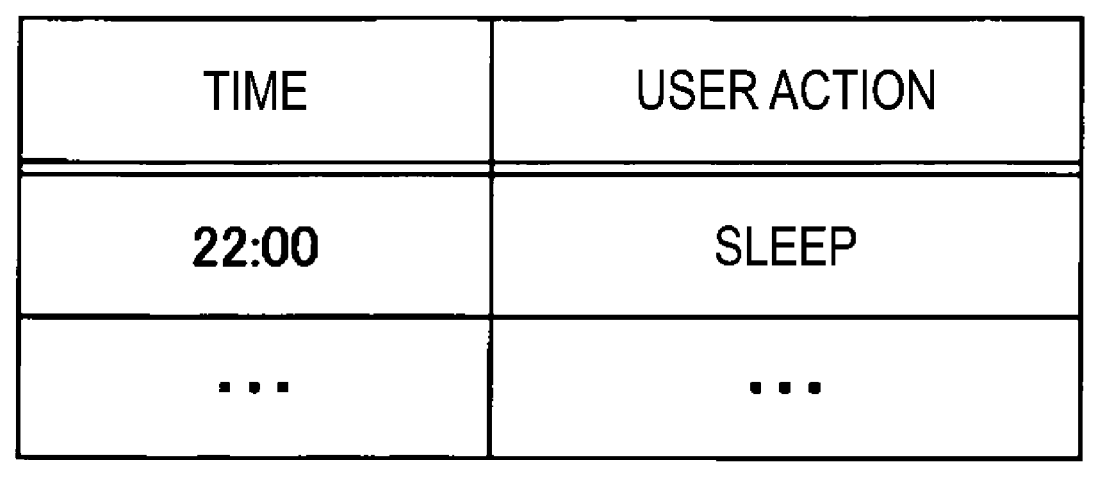

Next, an example of goal data in Example 1 will be described with reference to FIG. 3. FIG. 3 is a diagram illustrating an example of goal data in Example 1.

As illustrated in FIG. 3, the goal data in Example 1 is data in which a time is associated with a user action that the user has set as a goal at that time. In the example illustrated in FIG. 3, a time "22:00" and a user action "sleep" are associated with each other. This indicates that the user has a goal of performing a user action "sleep" at 22:00 (that is, a goal of going to bed at 22:00). Intervention measure data to be described below is data representing an optimal intervention measure for achieving this goal.

In this manner, the goal data in Example 1 is data in which a user's goal time is associated with a user action at that time. As will be described below, a reward for model-based reinforcement learning is defined by goal data.

Next, an example of intervention measure data in Example 1 will be described with reference to FIG. 4. FIG. 4 is a diagram illustrating an example of intervention measure data in Example 1.

As illustrated in FIG. 4, the intervention measure data in Example 1 is data in which a time, a user action, and an optimal intervention in a case where the user action is performed at the time are associated with each other. In the example illustrated in FIG. 4, a time "20:00", a user action "dinner", and an intervention "bath" are associated with each other, and the time "20:00", a user action "housework", and the intervention "bath" are associated with each other. This indicates that, in a case where the user action "dinner" or "housework" is observed at 20:00, an optimal intervention is the intervention for promoting a user action "bath".

Similarly, in the example illustrated in FIG. 4, a time "20:00", a user action "hobby", and an intervention "relax" are associated with each other, and the time "20:00", a user action "work", and the intervention "relax" are associated with each other. This indicates that, in a case where the user action "hobby" or "work" is observed at 20:00, an optimal intervention is the intervention for promoting a user action "relax".

Similarly, in the example illustrated in FIG. 4, a time "20:00", a user action "sleep", and an intervention "no intervention" are associated with each other. This indicates that, in a case where the user action "sleep" is observed at 20:00, an optimal intervention is "no intervention".

In this manner, the intervention measure data in Example 1 is data representing an optimal intervention for achieving a user's goal (that is, the detail of the optimal intervention) in a case where a certain user action is observed at a certain time.

<Processing Flow Executed by Observation Streamlining Apparatus 10 (Example 1)>

Figure 5:
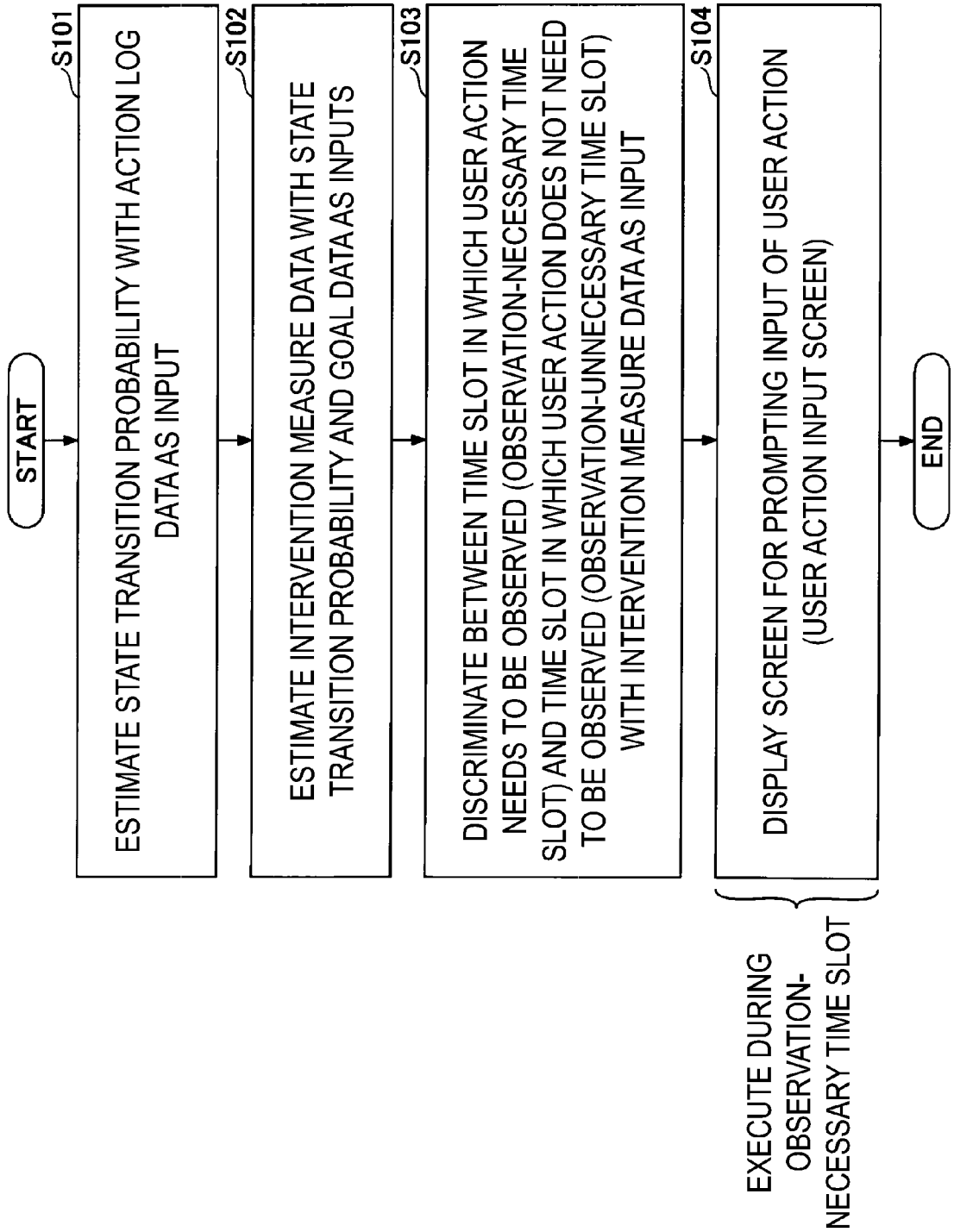
FIG. 5 is a flowchart illustrating an example of a processing flow executed by the observation streamlining apparatus in Example 1.

Next, a processing flow executed by the observation streamlining apparatus 10 in Example 1 will be described with reference to FIG. 5. FIG. 5 is a flowchart illustrating an example of a processing flow executed by the observation streamlining apparatus in Example 1.

First, the transition probability estimation unit 101 estimates a state transition probability in model-based reinforcement learning with action log data as an input (step S101). Note that the transition probability estimation unit 101 estimates a state transition probability by any method. For example, each user action (that is, each state) can be expressed as a discrete value, and thus the transition probability estimation unit 101 can estimate a state transition probability by counting combinations of a state $s_t$ and the next state $s_t+1$ at each time index t. Note that the state $s_t$ is a user action at a time index t and represents $s_t=1$ (sleep), $s_t=2$ (breakfast), $s_t=3$ (lunch), $s_t=4$ (dinner), $s_t=5$ (snack), $s_t=6$ (go to work), $s_t=7$ (work), $s_t=8$ (get off work), $s_t=9$ (housework), $s_t=10$ (exercise), $s_t=11$ (relax), $s_t=12$ (bath), $s_t=13$ (hobby), $s_t=14$ (drink), and $s_t=15$ (shopping).

Next, the learning unit 102 estimates intervention measure data with goal data, and the state transition probability estimated in step S101 described above as inputs (step S102). The learning unit 102 estimates a measure for increasing the sum of rewards defined by goal data as much as possible in the future (that is, an optimal measure) by a known method. Thereby, intervention measure data representing this measure is obtained. Here, the reward may be defined as larger value in a case where the user's goal has been achieved, but it is conceivable that a reward is defined to give, for example, a large positive value $r_g$ in a case where the user's goal has been achieved, 0 in the case of no intervention, and a negative value rites in other cases.

Specifically, for example, it is conceivable that $R_t(s_t, a_t, s_t+1)=r_g I(s_t+1=s_g, t+1=t_g)+r_{it_v} I\,(a_t\neq 16)$ is defined by setting a target state to be $s_g$, setting a time index representing a time slot in which the target state $s_g$ is achieved to be $t_g$, setting a reward $a_t$ the time index t to be $R_t$, and setting an intervention to be $a_t$. Here, $I(\cdot)$ is an indicator function. Note that $a_t=1, \ldots, 15$ are interventions for promoting user actions "sleep", "breakfast", "lunch", "dinner", "snack", "go to work", "work", "get off work", "housework", "exercise", "relax", "bath", "hobby", "drink", and "shopping", respectively, and $a_t=16$ indicates no intervention (none).

Note that a user may set a goal without designating a time (for example, a case where a period of time of a specific user action such as exercise is desired to be increased, or the like). In this case, it is conceivable that the reward $R_t$ is defined as $R_t(s_t, a_t, s_t+1)=r_g I(s_t+1=s_g)+r_{it_v} I\,(a_t\neq 16)$.

Next, the discrimination unit 103 discriminates whether each time slot is an observation-necessary time slot or an observation-unnecessary time slot with the intervention measure data estimated in step S102 described above as an input. (step S103). Specifically, the discrimination unit 103 determines a time slot in which an optimal intervention varies depending on a user action to be an observation-necessary time slot and determines a time slot in which an optimal intervention is identical regardless of a user action to be an observation-unnecessary time slot.

Figure 6:
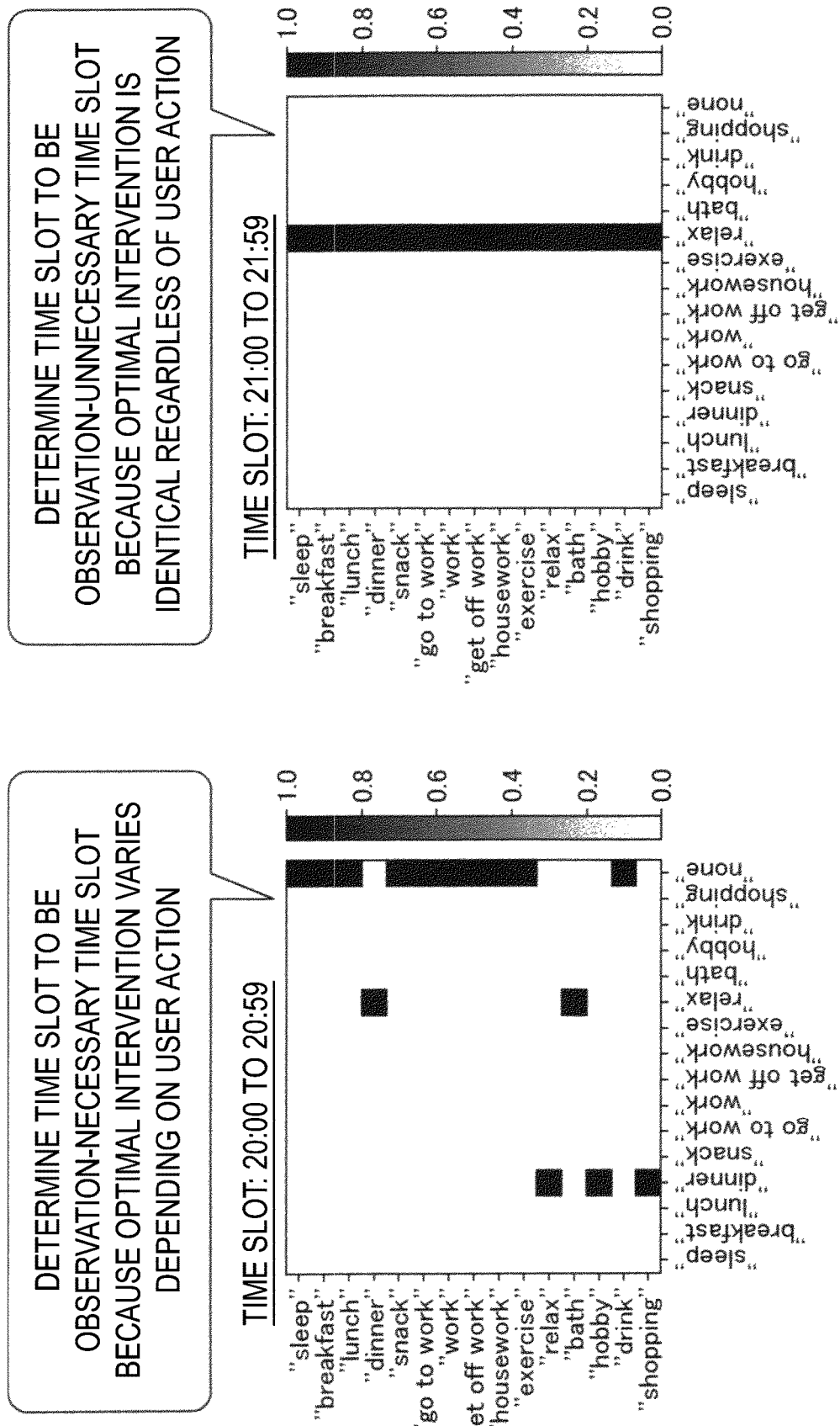
FIG. 6 is a diagram illustrating an example of discrimination between an observation-necessary time slot and an observation-unnecessary time slot.

Here, as an example, state transition probabilities visualized with shading are illustrated in FIG. 6 where states (States) $a_t$ times t=20 and 21 (that is, time slots of 20:00 to 20:59 and 21:00 to 21:59) are shown on a vertical axis, and optimal interventions (Actions) are shown on a horizontal axis.

In the left drawing of FIG. 6, it illustrates that, in a case where a state 520 is "dinner" or "bath", an optimal intervention am is "relax", in a case where the state 520 is "relax", "hobby", or "shopping", an optimal intervention am is "dinner", and in a case where the state 520 is something else, the optimal intervention am is "no intervention (none)". That is, when t=20, an optimal intervention $a_t$ varies depending on the state $s_t$ (that is, a user action). For this reason, a time slot of 20:00 to 20:59 represented by t=20 is determined to be an observation-necessary time slot. This is because it is necessary to observe a user action, because an optimal intervention varies depending on a user action.

On the other hand, in the right drawing of FIG. 6, an optimal intervention an is "relax" even when a state S21 is any user action. That is, when t=21, an optimal intervention $a_t$ is identical regardless of a state $s_t$ (that is, a user action). For this reason, a time slot of 21:00 to 21:59 represented by t=21 is determined to be an observation-unnecessary time slot. This is because it is not necessary to observe a user action, because an optimal intervention is identical regardless of a user action.

Figure 7:
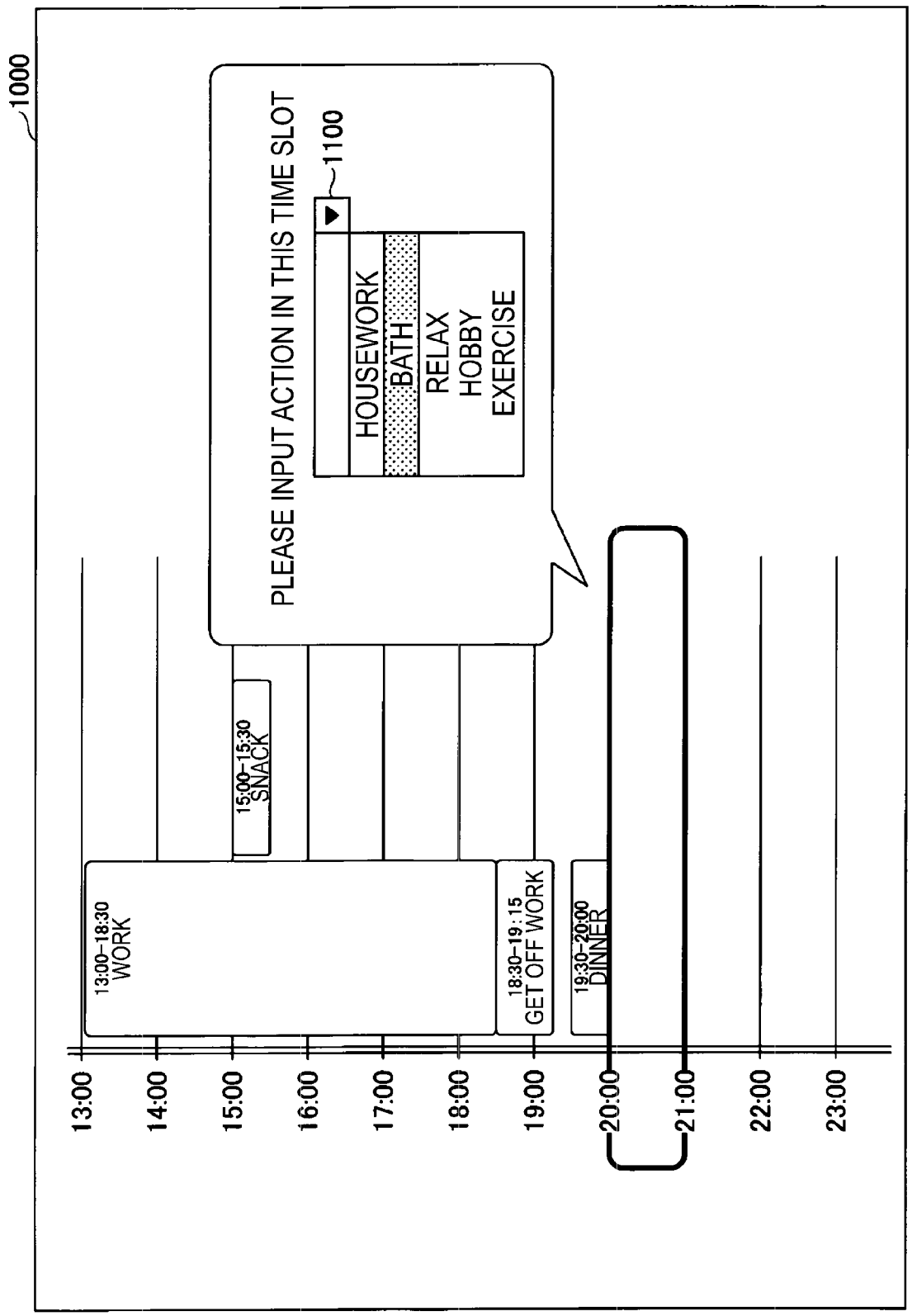
FIG. 7 is a diagram illustrating an example of a user action input screen.

Next, when the observation-necessary time slot arrives, the action acquisition promotion unit 104 displays a user action input screen on a terminal or the like which is used by the user (step S104). Here, an example of the user action input screen displayed on the terminal or the like is illustrated in FIG. 7. A user action input screen 1000 illustrated in FIG. 7 is a screen for promoting an input of a user action during a time slot of 20:00 to 20:59. The user action input screen 1000 illustrated in FIG. 7 includes a user action selection field 1100, and a user can input a user action during the time slot by selecting a desired user action in the user action selection field 1100. Information indicating a user action which is input by the user is transmitted to the observation streamlining apparatus 10, and an optimal intervention in a case where the user action is performed during the time slot is determined based on intervention measure data.

Note that the action acquisition promotion unit 104 may display the user action input screen on the terminal or the like when the observation-necessary time slot arrives (that is, in a case where the start time of the observation-necessary time slot has arrived), and may display the user action input screen on the terminal or the like during the observation-necessary time slot or at the end time of the observation-necessary time slot.

As described above, first, the observation streamlining apparatus 10 in Example 1 learns an optimal intervention measure by model-based reinforcement learning. Next, the observation streamlining apparatus 10 in Example 1 discriminates between the observation-necessary time slot in which it is necessary to observe a user action (State) and the observation-unnecessary time slot in which it is not necessary to observe a user action, in order to determine an optimal intervention (Action). Thereby, it is unnecessary to observe a user action during the observation-unnecessary time slot, and a user action only needs to be observed during the observation-necessary time slot, and thus it is possible to achieve the efficient observation of a user action.

Note that the inventor of the present application has confirmed that there is the observation-necessary time slot and the observation-unnecessary time slot by experiment. In the experiment, intervention measure data was estimated by the observation streamlining apparatus 10 in Example 1 using the actual action log data and goal data collected from a plurality of participants. At this time, visualized intervention measure data estimated from action log data and goal data collected from a participant A and visualized intervention measure data estimated from action log data and goal data collected from a participant B are illustrated in FIG. 8.

Figure 8:
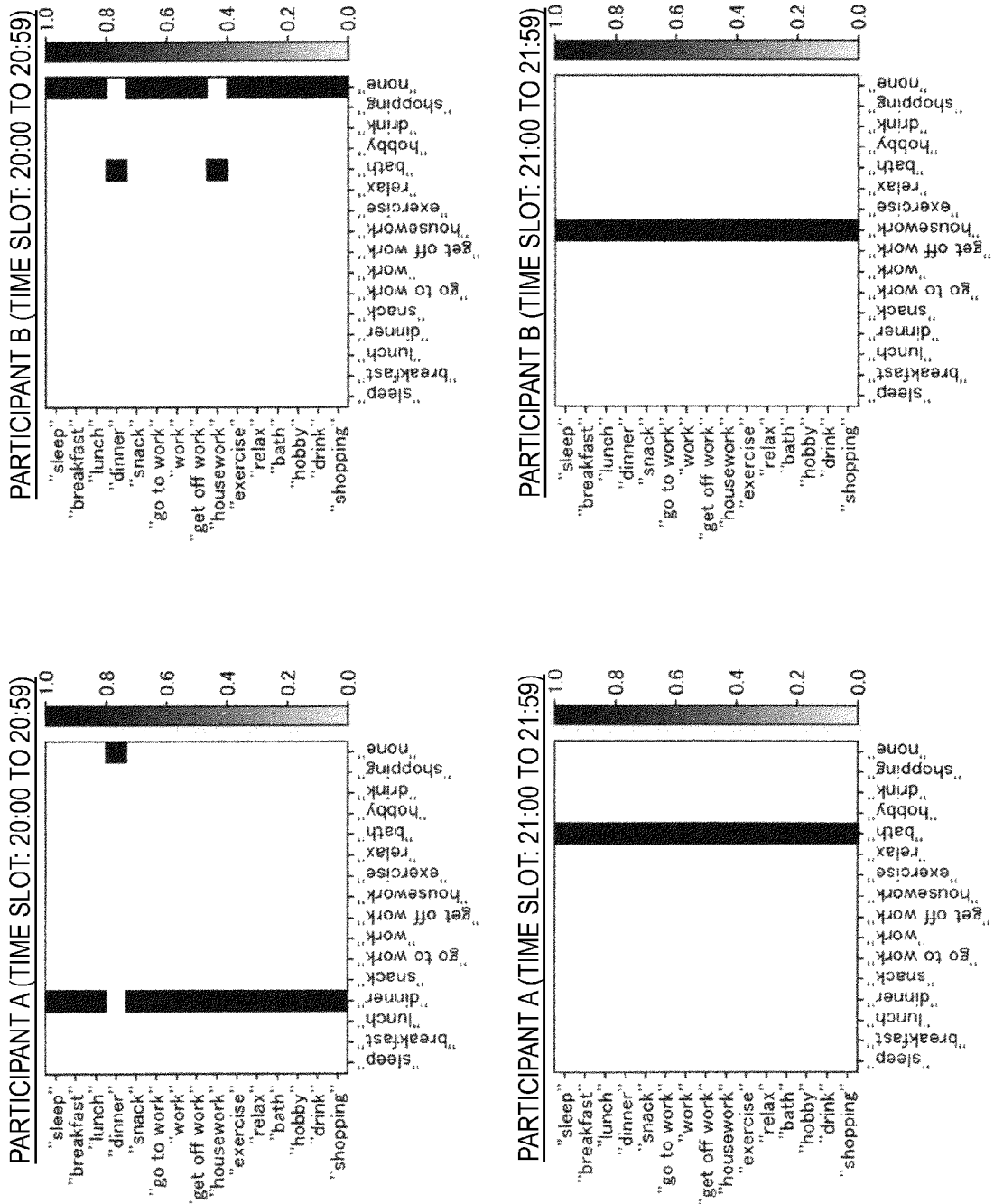
FIG. 8 is a diagram illustrating an example of experimental results indicating that there are an observation-necessary time slot and an observation-unnecessary time slot.

The upper left drawing of FIG. 8 illustrates that an optimal intervention $a_{20}$ is "no intervention (none)" in a case where a state 520 indicating a user action of the participant A at t=20 is "dinner", and an optimal intervention am is "dinner" in a case where the state 520 is not "dinner". Thus, in the case of the participant A, it can be said that a time slot of 20:00 to 20:59 represented by t=20 is the observation-necessary time slot.

On the other hand, in the lower left drawing of FIG. 8, even when a state S21 representing a user action of the participant A $a_t$ t=21 is any user action, an optimal intervention $a_{21}$ is "bath". Thus, in the case of the participant A, it can be said that a time slot of 21:00 to 21:59 represented by t=21 is the observation-unnecessary time slot.

Similarly, the upper right drawing of FIG. 8 illustrates that an optimal intervention am is "bath" in a case where a state 520 indicating a user action of the participant B $a_t$ t=20 is "dinner" or "housework", and an optimal intervention am is "no intervention (none)" in a case where the state 520 is not "dinner" or "housework". Thus, in the case of the participant B, it can be said that a time slot of 20:00 to 20:59 represented by t=20 is the observation-necessary time slot.

On the other hand, in the lower right drawing of FIG. 8, even when a state S21 representing a user action of the participant B $a_t$ t=21 is any user action, an optimal intervention $a_{21}$ is "housework". Thus, in the case of the participant B, it can be said that a time slot of 21:00 to 21:59 represented by t=21 is the observation-unnecessary time slot.

Example 2

Hereinafter, Example 2 will be described. In Example 2, a case where the efficiency of observation for determining an optimal intervention is improved by optimizing a timing at which an intervention is performed will be described. For example, Bayesian optimization or the like can be applied to optimize the timing.

Note that, in Example 2, differences from Example 1 will be mainly described, and the description of components similar to those in Example 1 will be omitted.

<Functional Configuration of Observation Streamlining Apparatus 10 (Example 2)>

Figure 9:
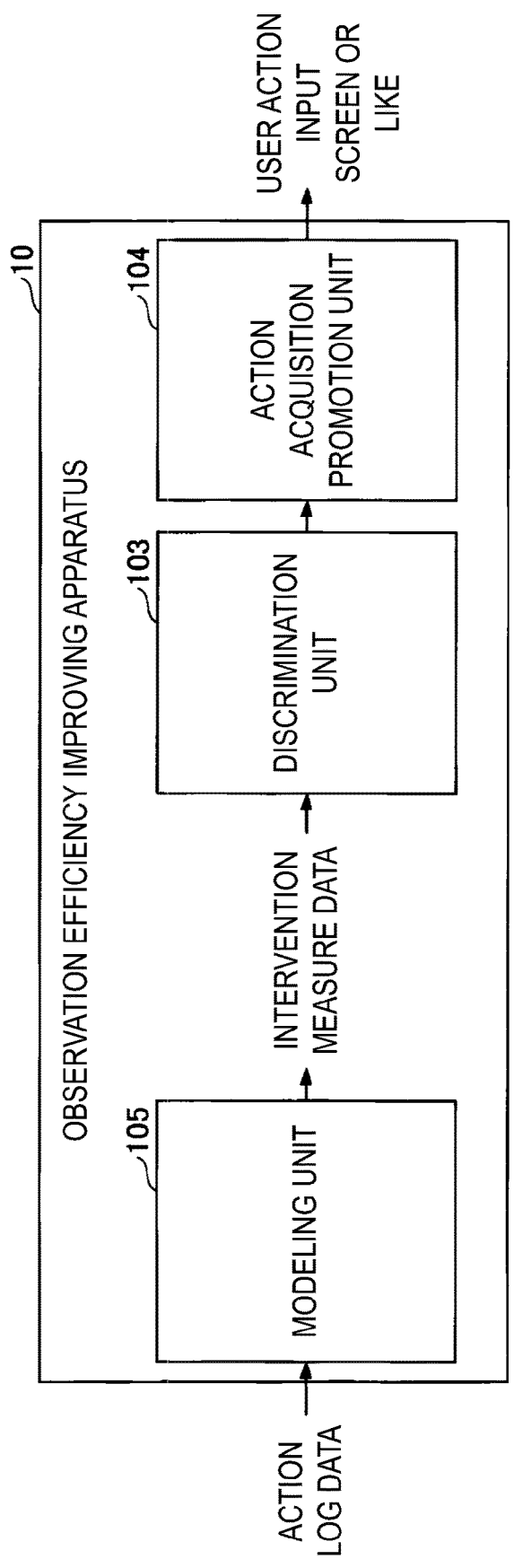
FIG. 9 is a diagram illustrating an example of a functional configuration of an observation streamlining apparatus in Example 2.

First, a functional configuration of an observation streamlining apparatus 10 in Example 2 will be described with reference to FIG. 9. FIG. 9 is a diagram illustrating an example of a functional configuration of the observation streamlining apparatus 10 in Example 2.

As illustrated in FIG. 9, the observation streamlining apparatus 10 in Example 2 includes a discrimination unit 103, an action acquisition promotion unit 104, and a modeling unit 105. Note that the action acquisition promotion unit 104 is similar to that in Example 1, and thus description thereof will be omitted.

The modeling unit 105 estimates intervention measure data representing a timing (time) at which an intervention is performed with action log data representing a log sequence of user actions and times collected in advance and a reward value in a case where a predetermined intervention is performed on this log sequence as an input. Note that the reward value is a value representing the goodness of intervention for achieving a predetermined goal.

The discrimination unit 103 discriminates between an observation-necessary time slot and an observation-unnecessary time slot in the same manner as in Example 1 with the intervention measure data estimated by the modeling unit 105 as an input.

Here, an example of action log data in Example 2 will be described with reference to FIG. 10. FIG. 10 is a diagram illustrating an example of action log data in Example 2.

As illustrated in FIG. 10, the action log data in Example 2 is data in which a log sequence of user actions and times is associated with a reward value in a case where a predetermined intervention is performed on the log sequence. In the example illustrated in FIG. 10, a log sequence "12:00 lunch, 13:00 work, 18:00 dinner" is associated with a reward value "30.5". This indicates that a reward (that is, the goodness of intervention for achieving a predetermined goal) is "30.5" in a case where a user has performed a predetermined intervention while performing a user action "dinner" after 18:00 on the assumption that the user is performing a user action "lunch" between 12:00 and 12:59 and that the user is performing a user action "work" between 13:00 and 17:59. This reward means that "a sleep time has extended by 30.5 hours", for example, in a case where a predetermined goal is "securing of a sleep time".

In this manner, the action log data in Example 2 is data in which a log sequence of user actions is associated with a reward in a case where a predetermined intervention has been performed on the log sequence.

Figure 11:
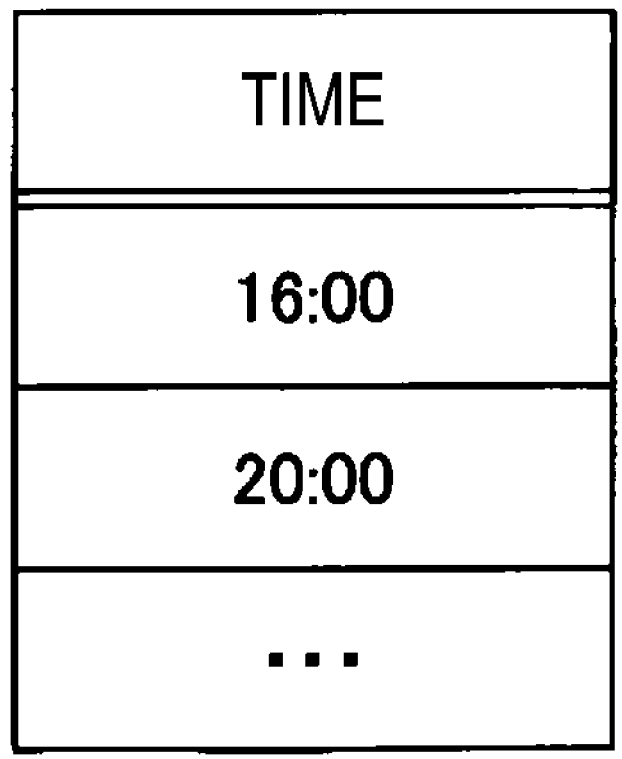
FIG. 11 is a diagram illustrating an example of intervention measure data in Example 2.

Next, an example of the intervention measure data in Example 2 will be described with reference to FIG. 11. FIG. 11 is a diagram illustrating an example of intervention measure data in Example 2.

As illustrated in FIG. 11, the intervention measure data in Example 2 is time-series data indicating an optimal intervention timing. In the example illustrated in FIG. 11, the intervention measure data includes times "16:00" and "20:00". This indicates that "16:00" and "20:00" are optimal intervention timings for performing a predetermined intervention.

In this manner, the intervention measure data in Example 2 is time-series data representing an optimal intervention timing.

Figure 12:
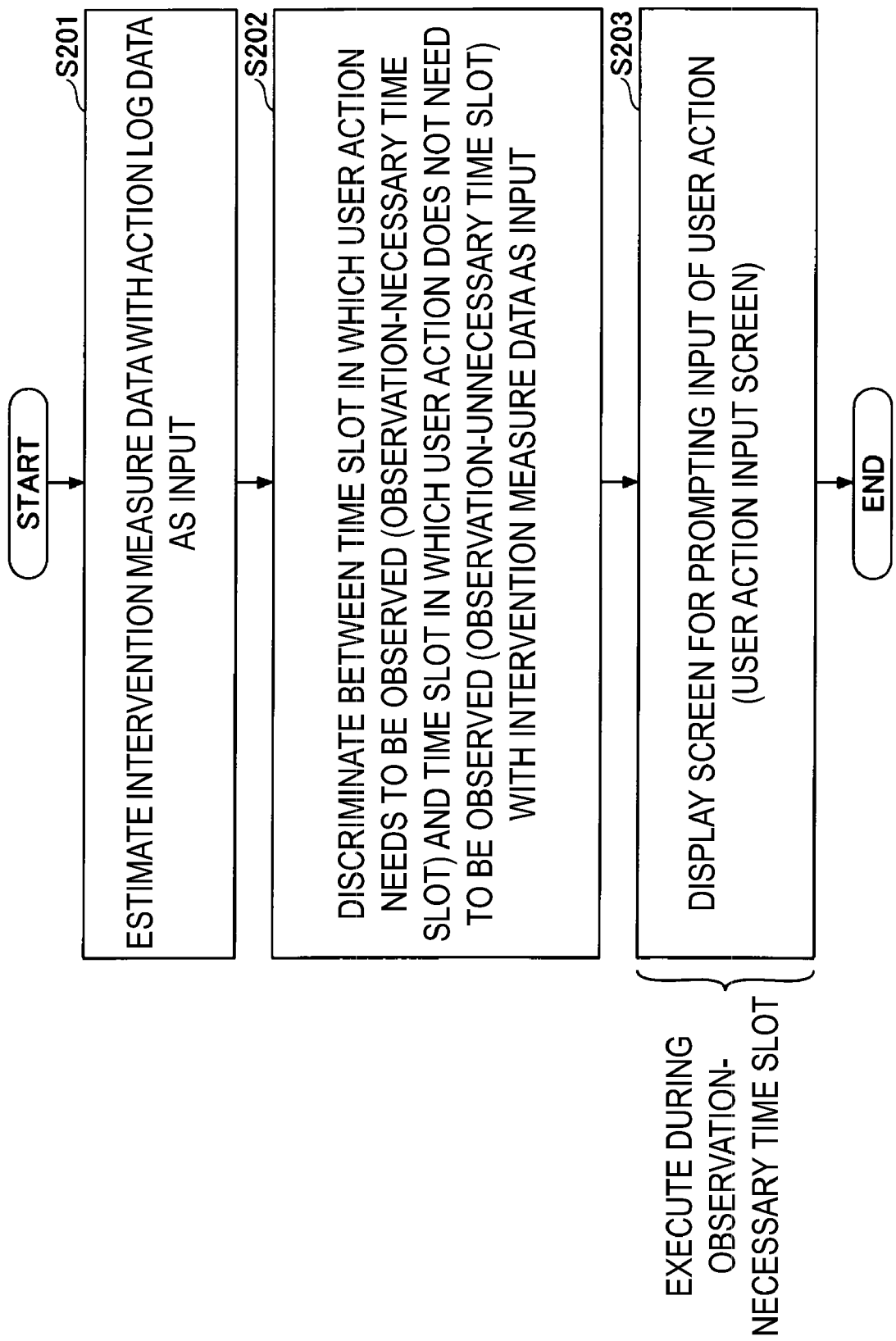
FIG. 12 is a flowchart illustrating an example of a processing flow executed by the observation streamlining apparatus in Example 2.

Processing Flow Executed by Observation Streamlining Apparatus 10 (Example 2) Next, a processing flow executed by the observation streamlining apparatus 10 in Example 2 will be described with reference to FIG. 12. FIG. 12 is a flowchart illustrating an example of a processing flow executed by the observation streamlining apparatus in Example 2.

First, the modeling unit 105 estimates intervention measure data with action log data as an input (step S201). Note that, as described above, in Example 2, the action log data is data representing a log sequence of user actions and times and a reward value in a case where a predetermined intervention is performed on the log sequence, and the intervention measure data is data representing an optimal intervention timing.

Here, the modeling unit 105 estimates intervention measure data by modeling a correspondence relationship between the log sequence of user actions and times and a reward value thereof. A Gaussian process is widely used for modeling, but the modeling can also be achieved by other methods such as a Gaussian process using a Poisson process for noise. A vector having a fixed length is mainly handled as an input in a Gaussian process. However, in a case where the number of user actions and times included in the log sequence is not a fixed length as in the present example, a linear function kernel is used. Modeling is performed in this manner, and thus it is possible to predict a reward in a case where a predetermined intervention will be performed at a future time. Thus, a time at which a reward is largest is output as intervention measure data. Note that, for the linear function kernel, reference will be made to, for example, "Park, Il Memming, et al. "Kernel methods on spike train space for neuroscience: a tutorial." IEEE Signal Processing Magazine 30.4 (2013): 149-160" and the like.

Next, the discrimination unit 103 discriminates between an observation-necessary time slot and an observation-unnecessary time slot with the intervention measure data estimated in step S201 described above as an input (step S202). Because a user action from the present time to an intervention timing does not need to be observed, the discrimination unit 103 determines a time slot from the present time to the intervention timing to be the observation-unnecessary time slot and determines the other time slots to be the observation-necessary time slot.

Next, similarly to step S104 in FIG. 5, the action acquisition promotion unit 104 displays a user action input screen on a terminal or the like which is used by a user when the observation-necessary time slot arrives (step S203).

As described above, the observation streamlining apparatus 10 in Example 2 estimates an optimal intervention timing as an intervention measure by Bayesian optimization or the like and then determines a time slot from the present time to the optimal intervention timing to be the observation-unnecessary time slot. Thereby, similarly to Example 1, a user action does not need to be observed during the observation-unnecessary time slot, and a user action only need be observed during the observation-necessary time slot, and thus it is possible to achieve the efficient observation of a user action.

Hardware Configuration

Figure 13:
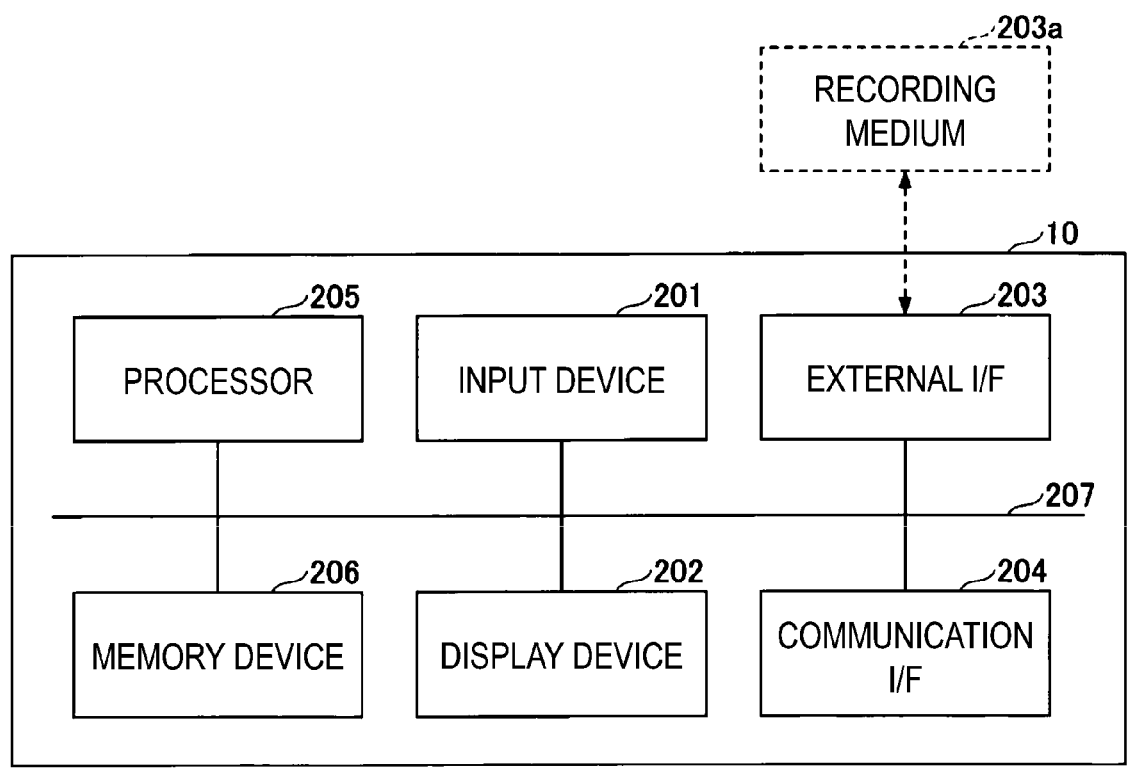
FIG. 13 is a diagram illustrating an example of a hardware configuration of an observation streamlining apparatus according to an embodiment.

Finally, a hardware configuration of the observation streamlining apparatus 10 according to the present embodiment will be described with reference to FIG. 13. FIG. 13 is a diagram illustrating an example of a hardware configuration of the observation streamlining apparatus 10 according to the embodiment.

As illustrated in FIG. 13, the observation streamlining apparatus 10 according to the present embodiment is a general-purpose computer or computer system, and includes an input device 201, a display device 202, an external I/F 203, a communication I/F 204, a processor 205, and a memory device 206. The pieces of hardware are communicably connected via a bus 207.

The input device 201 is, for example, a keyboard, a mouse, or a touch panel. The display device 202 is, for example, a display or the like. Note that the observation streamlining apparatus 10 does not need to include at least one of the input device 201 or the display device 202.

The external I/F 203 is an interface for an external device. Examples of the external device include a recording medium 203a and the like. The observation streamlining apparatus 10 can perform reading, writing, and the like on the recording medium 203a via the external I/F 203. In the recording medium 203a, for example, one or more programs for implementing the functional units (for example, the transition probability estimation unit 101, the learning unit 102, the discrimination unit 103, and the action acquisition promotion unit 104 in the case of Example 1, and the discrimination unit 103, the action acquisition promotion unit 104, and the modeling unit 105 in the case of Example 2) included in the observation streamlining apparatus 10 may be stored.

Note that examples of the recording medium 203a include a compact disc (CD), a digital versatile disk (DVD), a secure digital memory card (SD memory card), a universal serial bus (USB) memory card, and the like.

The communication I/F 204 is an interface for connecting the observation streamlining apparatus 10 to a communication network. Note that one or more programs for implementing the functional units of the observation streamlining apparatus 10 may be acquired (downloaded) from a predetermined server device or the like via the communication I/F 204.

The processor 205 is any of various calculation devices such as a central processing unit (CPU) or a graphics processing unit (GPU). For example, the functional units included in the observation streamlining apparatus 10 are implemented by processing for causing the processor 205 to execute one or more programs stored in the memory device 206.

The memory device 206 is any of various storage devices such as a hard disk drive (HDD), a solid state drive (SSD), a random access memory (RAM), a read only memory (ROM), and a flash memory. Note that various pieces of data (for example, goal data, action log data, intervention measure data, and the like) are stored in, for example, the memory device 206.

The observation streamlining apparatus 10 according to the present embodiment has the hardware configuration illustrated in FIG. 13 and thus can implement the above-mentioned various processing operations. Note that the hardware configuration illustrated in FIG. 13 is an example, and the observation streamlining apparatus 10 may have another hardware configuration. For example, the observation streamlining apparatus 10 may include a plurality of processors 205 or may include a plurality of memory devices 206.

The present disclosure is not limited to the above-described embodiment disclosed specifically, and various modifications or changes, combinations with known techniques, and the like can be made without departing from the recitation of claims.

REFERENCE SIGNS LIST

10 Observation streamlining apparatus
101 Transition probability estimation unit
102 Learning unit
103 Discrimination unit
104 Action acquisition promotion unit
105 Modeling unit

The invention claimed is:

1. An observation streamlining apparatus comprising:
one or more computers each including a memory and a processor configured to:
discriminate between an observation-necessary time slot and an observation-unnecessary time slot with an intervention measure including at least a time when a predetermined intervention is performed on a user as an input, the observation-necessary time slot indicating a time slot when a user's action or state needs to be observed, and the observation-unnecessary time slot indicating a time slot when the user's action or state does not need to be observed; and
execute predetermined processing for observing the user's action or state when the observation-necessary time slot arrives.

2. The observation streamlining apparatus according to claim 1, wherein the intervention measure includes the time, the user's action or state at the time, and a detail of the intervention, and
the memory and the processor are further configured to
determine a time slot when the detail of the intervention varies depending on the user's action or state to be the observation-necessary time slot, and
determine a time slot when the detail of the intervention is identical regardless of the user's action or state to be the observation-unnecessary time slot.

3. The observation streamlining apparatus according to claim 1, wherein the time included in the intervention measure is a time indicating an optimal timing for performing the intervention, and
the memory and the processor are further configured to
determine a time slot from a present time to the time indicating the optimal timing to be the observation-unnecessary time slot, and
determine a time slot other than the observation-unnecessary time slot to be the observation-necessary time slot.

4. The observation streamlining apparatus according to claim 1, wherein the predetermined processing includes at least one of processing for displaying a screen for promoting an input of the user's action or state on a terminal used by the user, processing for outputting an alert for promoting an input of the user's action or state on the terminal, or processing of acquiring the user's action or state by a sensor.

5. An observation streamlining method executed by a computer including a memory and a processor, the method comprising:
discriminating between an observation-necessary time slot and an observation-unnecessary time slot with an intervention measure including at least a time when a predetermined intervention is performed on a user as an input, the observation-necessary time slot indicating a time slot when a user's action or state needs to be observed, and the observation-unnecessary time slot indicating a time slot when the user's action or state does not need to be observed; and
executing predetermined processing for observing the user's action or state when the observation-necessary time slot arrives.

6. A non-transitory computer-readable recording medium having computer-readable instructions stored thereon, which when executed cause a computer including a memory and a processor to execute respective operations in the observation streamlining apparatus according to claim 1.

* * * * *